United States Patent
Morisseau et al.

(10) Patent No.: US 12,342,031 B2
(45) Date of Patent: Jun. 24, 2025

(54) OUT OF BAND CONTROL FOR LEGACY SET TOP BOXES

(71) Applicant: ARRIS Enterprises LLC, Suwanee, GA (US)

(72) Inventors: Michael R. Morisseau, Lowell, MA (US); Clarke V. Greene, Middletown, CT (US); David Bowler, Stow, MA (US); Bruce Pratt, Bedford, NH (US)

(73) Assignee: ARRIS Enterprises LLC, Suwanee, GA (US)

( * ) Notice: Subject to any disclaimer, the term of this patent is extended or adjusted under 35 U.S.C. 154(b) by 113 days.

(21) Appl. No.: 17/975,282

(22) Filed: Oct. 27, 2022

(65) Prior Publication Data

US 2023/0137077 A1    May 4, 2023

Related U.S. Application Data

(60) Provisional application No. 63/272,982, filed on Oct. 28, 2021.

(51) Int. Cl.
| | | |
|---|---|---|
| *H04N 21/426* | (2011.01) | |
| *A61B 5/349* | (2021.01) | |
| *A61B 5/366* | (2021.01) | |
| *H04N 21/61* | (2011.01) | |

(52) U.S. Cl.
CPC ........... *H04N 21/426* (2013.01); *A61B 5/349* (2021.01); *A61B 5/366* (2021.01); *H04N 21/42676* (2013.01); *H04N 21/6118* (2013.01)

(58) Field of Classification Search
CPC ............. H04N 21/426; H04N 21/6118; H04N 21/64784; H04N 21/6168; H04N 21/42676
See application file for complete search history.

(56) References Cited

U.S. PATENT DOCUMENTS

| | | | |
|---|---|---|---|
| 8,537,861 B2* | 9/2013 | Howard | H04N 7/22 370/480 |
| 9,247,310 B2* | 1/2016 | Chapman | H04N 21/6118 |
| 2013/0276047 A1* | 10/2013 | Chapman | H04N 21/6547 725/111 |
| 2016/0295251 A1* | 10/2016 | Cloonan | H04N 21/615 |
| 2017/0142493 A1* | 5/2017 | Howe | H04L 69/08 |
| 2020/0329262 A1* | 10/2020 | Bonen | H04N 21/2662 |
| 2023/0090396 A1* | 3/2023 | Thompson | H04L 43/0876 375/257 |

* cited by examiner

Primary Examiner — Pinkal R Chokshi
(74) Attorney, Agent, or Firm — Chernoff, Vilhauer, McClung & Stenzel, LLP (57) ABSTRACT

A system for out of band control for legacy set top boxes in which an out-of-band (OOB) downstream signal containing control information for consumer premises equipment is transmitted to an end-of-line device, which converts it to an upstream OOB signal, then sends the upstream OOB signal in an upstream direction.

8 Claims, 5 Drawing Sheets

OUT OF BAND CONTROL FOR LEGACY SET TOP BOXES

CROSS REFERENCE TO RELATED APPLICATIONS

This application claims the benefit of U.S. Provisional Patent Application Ser. No. 63/272,982 filed Oct. 28, 2021.

BACKGROUND

The subject matter of this application relates to out of band control for legacy set top boxes.

Modern CATV delivery systems provide to their customers not only the broadcast television content (video plane) historically associated with cable delivery networks, but also data services (data plane) such as Internet services, certain video-on-demand, and other data communications either desired or necessary for providing customer services. The evolution of the architectures to deliver these respective video plane and data plane services has traditionally been disconnected, since traditional radio frequency (RF) combiner networks in a headend allowed video and data streams to have a fair degree of independence during delivery of both video and data. The CATV delivery systems provide channel mappings for broadcast video services to customer premise equipment, such as various forms of set top boxes. As the CATV delivery systems have evolved, including distributed and non-distributed architectures, different bands of frequencies are used for upstream and downstream traffic, which results in managing the desired channel mapping and other control functionality for broadcast video services across a variety of different customer premise equipment to be problematic.

What is desired, therefore, is an efficient manner of managing the channel mapping and other control functionality for QAM based video services, including broadcast and narrowcast QAM video services across different customer premise equipment.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION

One exemplary type of cable television system is a distributed access architecture (DAA). Distributed access architectures may include Remote-Physical (R-PHY) architectures that relocate physical (PHY) devices downstream into the network while retaining the control layer (MAC) layer in the headend, as well as R-MACPHY architectures that relocate both the PHY and MAC layers downstream into the network and R-OLT architectures that relocate optical line terminals (OLT) in passive optical networks (PON) to a remote location, as well as many other variations. An R-PHY architecture, which remotely locates a physical device (PHY) that converts optical digital signals to radio frequency (RF) signals such as a quadrature amplitude modulated (QAM) signal, will be used to describe the embodiments disclosed in this specification, but those of ordinary skill in the art will appreciate that the disclosures herein may be employed with other DAA architectures and/or remote devices. Further, the embodiments disclosed herein in this specification are likewise applicable to non-DAA architectures.

Figure 1:
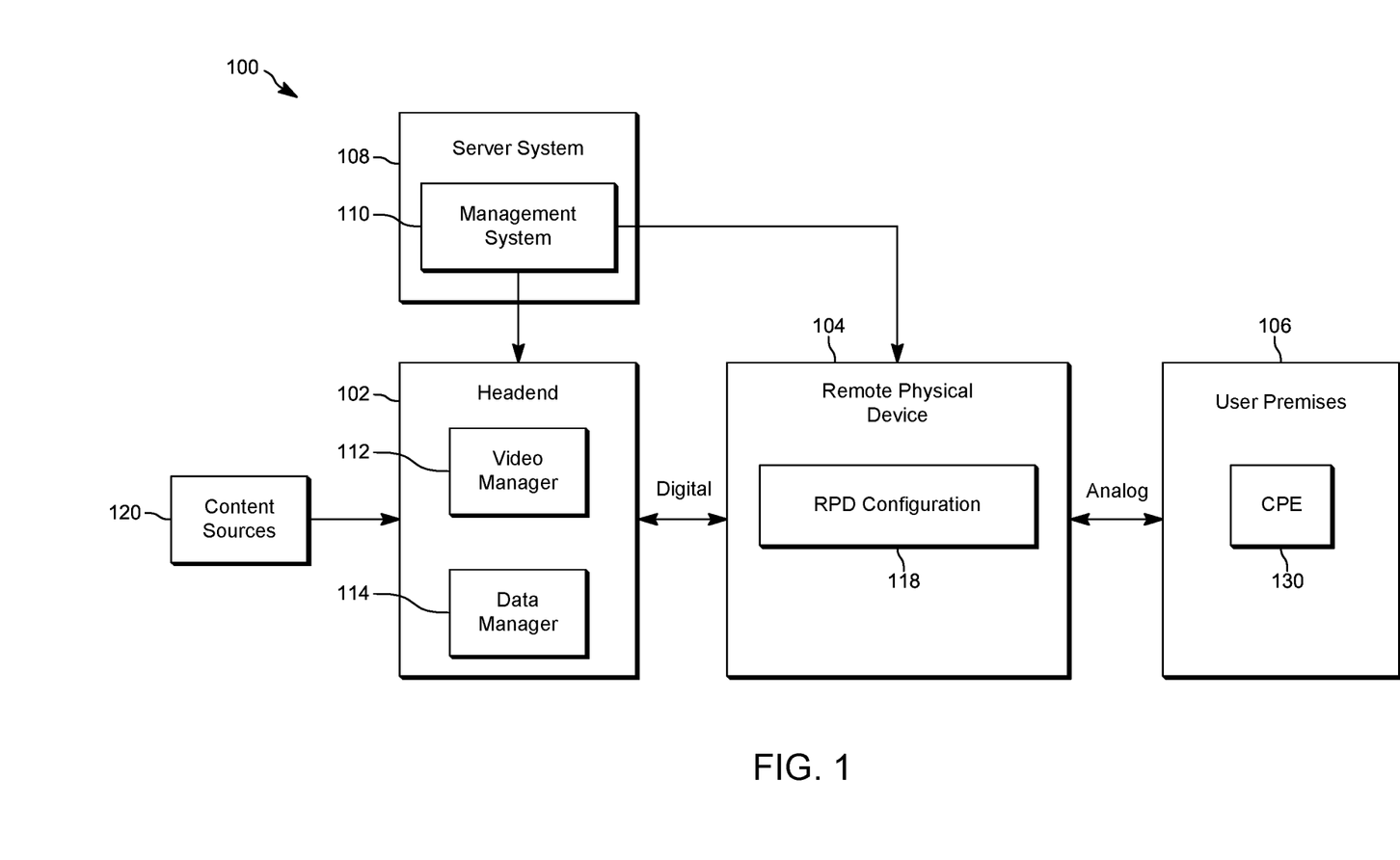
FIG. 1 illustrates an exemplary system for delivering data and video in a distributed architecture.

FIG. 1 depicts a simplified system 100, simply for purposes of illustration, capable of being used to implement a technique for delivering data and video according to some embodiments. The system 100 includes a headend 102, a remote physical device 104, user premises 106, and a server system 108. The system 100 may be a distributed access architecture as discussed above where digital optical components are used to replace analog optical components between the headend 102 and the remote physical device 104, which allows the physical components to perform the analog to digital (and RF) conversion and to be configured deeper in the network, closer to the user premises 106. The headend 102 may deliver video and data to user premises 106 using the remote physical device 104. Although a single user premises 106 and a single remote physical device 104 are shown, the remote physical device 104 may be coupled to multiple user premises 106. Additionally, the system 100 may include multiple remote physical devices 104 that are coupled to different sets of user premises 106. It is noted that traditional non-DAA analog distribution system may continue to coexist with the DAA illustrated. It is noted that traditional non-DAA architectures may likewise be used, as desired.

The headend 102 may receive video and data from content sources 120. A video manager 112 may manage the video delivery to the user premises 106 and a data manager 114 may manage the data delivery to the user premises 106. In some embodiments, the headend 102 may deliver both video and data to the user premises 106 via the same frequency spectrum. For example, the RF frequency spectrum may include an upstream frequency range and a downstream frequency range. The downstream frequency range may deliver both video and data downstream from the headend 102 to the user premises 106 at different frequencies. Similarly, the upstream frequency range delivers video and data upstream from the user premises 106 to the headend 102. The headend 102 may send the video and data signal via a digital network, such as via an optical signal. The remote physical device 104 may receive the digital signal and convert the signal to analog, such as to an RF signal. In the upstream direction, the remote physical device 104 receives analog video or data signaling from the user premises 106, converts the analog video or data signaling to a digital signal, and sends the digital signal to the headend 102.

The video manager 112 may use an RPD configuration 118 to insert video and data into a digital signal that is sent to the remote physical device 104. The remote physical device 104 then converts the video into analog at the corresponding frequencies and sends the analog signal to the user premises 106.

The RPD configuration 118 may be a list of addresses that pertain to video delivery. For example, the addresses may be multicast addresses for video streams. The video manager 112 uses information that is associated with video streams received at the headend 102 to determine which video to insert into the digital signal that is sent to the remote physical device 104. For example, the headend 102 receives various video streams based on a legacy video delivery through a legacy video network (e.g., a network that creates video streams and performs the QAM RF conversion at the headend 102). The video manager 112 inserts the appropriate video into the digital signal with information about the desired frequency placement for the specific RPD configuration 118 and provides the video to the specific remote physical device 104.

The server system 108 includes a management system 110 that can define the suitable configuration for the video delivery for the headend 102. The management system 110 may also define the suitable configuration of the RPD configuration 118 for the video delivery for the remote physical device 104.

As it may be observed the user premises 106 may include consumer premises equipment (CPE) 130 in the form of cable modems and/or set top boxes and/or television with decrypting card (or otherwise) at the user premises 106. Such consumer premises equipment are distributed across cable systems ranging from thousands of devices to hundreds of thousands of devices to tens of millions of devices to receive and render broadcast video services. In some cases, such consumer premises equipment may be one way receiving devices that are not capable of transmitting data or otherwise to the network. In other cases, such consumer premises equipment may further be capable of transmitting data or otherwise to the network. In yet other cases, such consumer premises equipment may be capable of receiving other types of video streams, such as those suitable for linear broadcasts, conditional access, video on demand, switched digital video, and/or advertisement insertion.

The headend 102 in combination with the remote physical device 104 (if included in the network topology) are often capable of providing (1) video stream distributions where one or more of the video streams are constructed based on selections by the viewer, in a manner together with, (2) the broadcast of more traditional video streams, such as legacy networks (e.g., ABC, CBS, NBC, CNN, PBS, etc.) where the video streams are not constructed based on selections by the viewer. Both video streams are provided by the headend 102 to the remote physical device 104 and to the user premises as an analog signal on a coaxial cable. Accordingly, the video stream is provided by the headend 102 to the user premises 106 and the CPEs 130. When the viewer selects a channel in a traditional broadcast video stream the consumer premises equipment tunes to the selected channel of the traditional broadcast video stream. In this manner, the headend 102 is capable of providing traditional broadcast video streams to the consumer premises equipment that are not capable of making particular requests. In the event that the consumer premises equipment is capable to making requests to the headend 102 for particular video streams, the requested video stream may be provided to the consumer premises equipment through a coordination of video stream placement and consumer premises equipment tuning by a system, such as a switched digital video system.

The DOCSIS protocol is often used to send digital video and data between the headend and the customer premise equipment (e.g., cable modem and/or set top box). For many customer premise equipment, a control channel consists of an out-of-band (OOB) carrier located at or near 75 MHz in the downstream spectrum. The out-of-band (OOB) carrier may be located at frequencies, such as in the range of 70 MHz to 130 MHz. The control channel includes various data for providing control information to the customer premise equipment, such as channel maps, program guides, and code images. As users send more data upstream, it is desirable for cable system operators to increase the upstream capacity.

Figure 2:
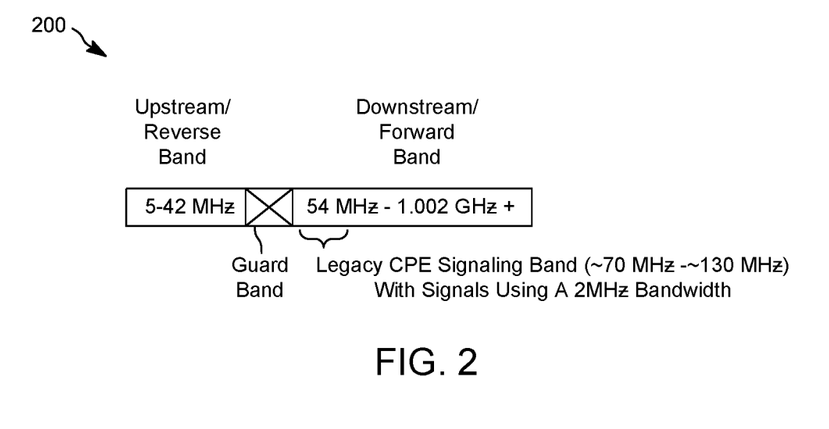
FIG. 2 illustrates a frequency spectrum for a legacy cable network.

Referring to FIG. 2, the traditional RF spectrum 200 for use with the DOCSIS protocol has a 5-42 MHz upstream band in the United States and a 5-65 MHz band in Europe, a guard band, and a downstream band. The downstream band is 54 MHz on the low side to 550 MHz, 750 MHz, 862 MHz, 1002 MHz, or greater on the high side. As previously mentioned, legacy customer premise equipment are programmed via an out of band (OOB) 2 MHz control channel in the 70-130 MHz region of the forward band. In some cases, the OOB control channel ranges from 2-6 MHz channel bandwidth, which may include three 2 MHz control channels. The OOB control frequency is normally set to 75+−1 MHz which is at a gap between legacy analog television channels four and five.

Figure 3:
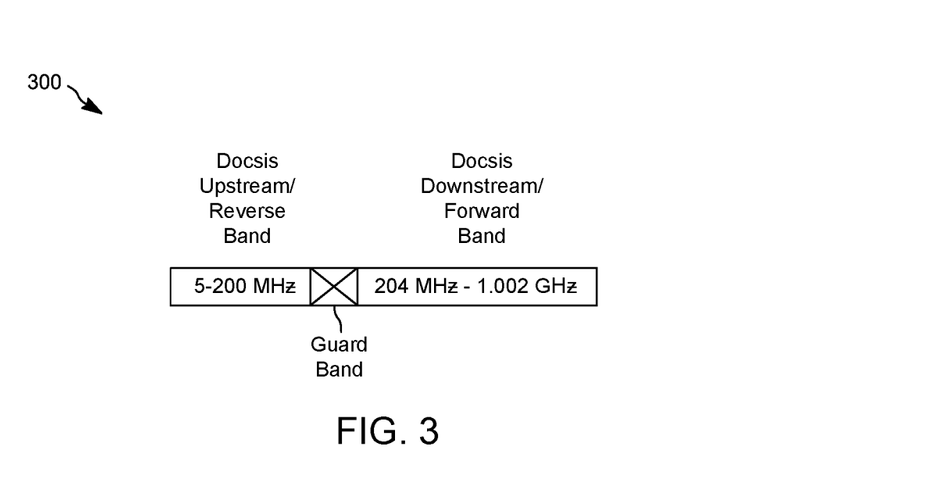
FIG. 3 illustrates a frequency spectrum for a high split cable network.

Referring to FIG. 3, a high split RF spectrum 300 for use with the DOCSIS protocol, or otherwise, extends the DOCSIS upstream bandwidth. The high split RF spectrum 300 extends the upstream from 5-42 MHz to 5-200 MHz (or similar frequency) and modifies the downstream spectrum from 54 MHz to 204 MHz as the lower frequency (or similar frequency).

The high split of the RF spectrum includes a substantial drawback when used together with legacy consumer premise equipment, since the high split eliminates the 70-130 MHz legacy downstream OOB control channel used by legacy consumer premise equipment. Accordingly, in order to make use of the high split which allocates additional upstream bandwidth all of the existing legacy consumer premise equipment would need to be replaced. Rather than having to replace all existing legacy consumer premise equipment, in order to support the OOB control channel, it is desirable to devise other techniques for providing the out of band signaling to the legacy customer premise equipment with the high split network.

Figure 4:
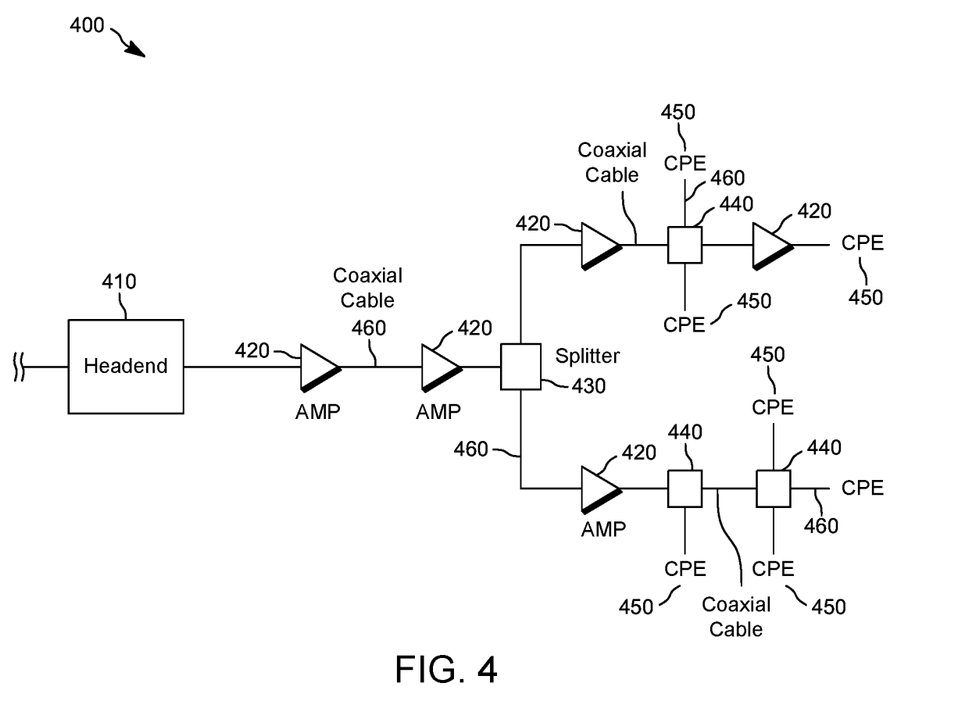
FIG. 4 illustrates a cable network with amplifiers, splitter(s), taps, and consumer premise equipment.

Referring to FIG. 4, a simplified cable network 400 is illustrated. The network 400 includes a set of components that are arranged at various positions within the network depending on the particular topology. A headend 410 sends data to the network and receives data from the network. The network includes one or more amplifiers 420, one or more splitters 430, one or more taps 440, etc., to provide data to and receive data from customer premise equipment 450. The components are interconnected together by coaxial cables 460. In many networks, optical fibers are also used between the headend 410 and an optical node in the network.

Figure 5:
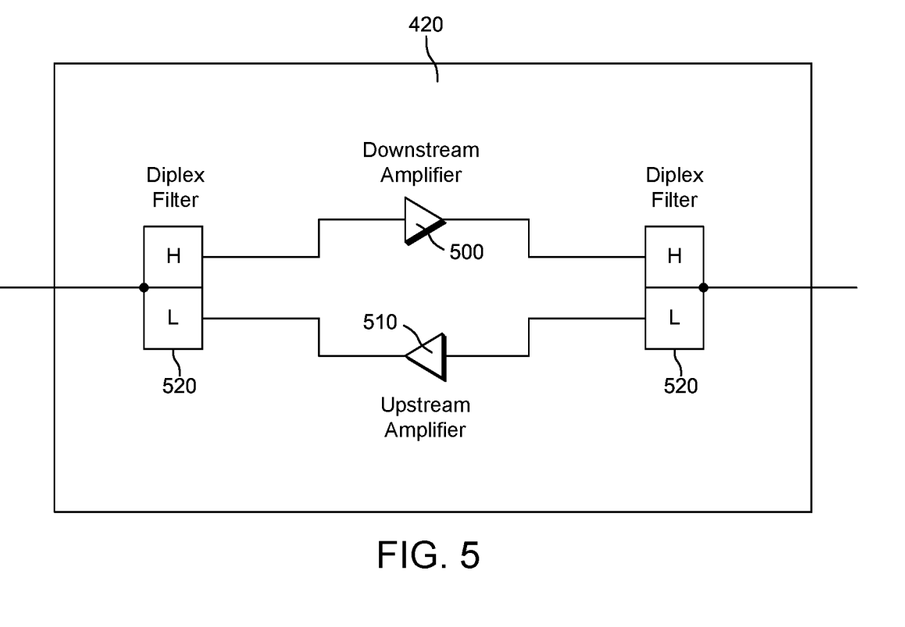
FIG. 5 illustrates an amplifier.

Referring also to FIG. 5, each of the amplifiers 420 are preferably a two-way amplifier that includes a downstream amplifier circuitry 500 and upstream amplifier circuitry 510. The inputs to the amplifier also preferably include respective diplex filters (high and low) 520. In this manner, the downstream data is filtered by the diplex filters 520 and amplified by the downstream amplifier 500. In this manner, the upstream data is filtered by the diplex filters 520 and amplified by the upstream amplifier 510. The range of the downstream amplifier 500, in combination with the diplex filters 520, are preferably selected to correspond to the range of frequencies for the high split architecture, such as for example, 204 MHz to 1.2 GHz. The range of the upstream amplifier 510 in combination with the diplex filters 520, are preferably selected to correspond to the range of frequencies for the high split architecture, such as for example, 5 MHz to 200 MHz. Other frequency ranges may likewise be used, as desired.

The downstream amplifier could be modified to further include the capability of amplifying and passing through the out of band frequency (e.g., 75 MHz) together with the downstream frequency range (e.g., 204 MHz to 1.2 GHz). The downstream diplex filters could be modified to further include the capability of passing through the out of band frequency (e.g., 75 MHz) together with the downstream frequency range (e.g., 204 MHz to 1.2 GHz). In this manner, the OOB frequency carrying the control channel data can be passed through the amplifier to the customer premise equipment. However, the passing of a narrow band of frequencies together with the broad range of frequencies tends to result in substantially increased complexity together with added complexities associated with signal integrity due to the narrow passband.

The upstream amplifier could be modified to further include the capability of blocking the out of band frequency (e.g., 75 MHz) within the upstream frequency range (e.g., 5 MHz to 200 MHz). Also, the diplex filters could be modified to further include the capability of blocking the out of band frequency (e.g., 75 MHz) within the upstream frequency range (e.g., 5 MHz to 200 MHz). In this manner, the OOB frequency carrying the control channel data can be prevented from passing through the amplifier in the upstream direction. However, the blocking of a narrow band of frequencies within the broad range of frequencies tends to result in substantially increased complexity together with added complexities associated with signal integrity associated with the narrow blocked band. Also, the blocking of the OOB frequency in the upstream path is likely necessary to prevent the upstream OOB frequency from being subsequently amplified in the downstream path.

Unfortunately, such an amplifier modification including diplex filters requires switching out of a multitude of amplifiers within the network, with the added expense and disruption to customers. In a similar manner, the splitters 430 may need to be modified to accommodate the providing the OOB frequency in the downstream path while rejecting the OOB frequency in the upstream path. In a similar manner, the taps 440 may need to be modified to accommodate the providing the OOB frequency in the downstream path while rejecting the OOB frequency in the upstream path. Unfortunately, such modifications to the splitters and/or the taps, in addition to other components in the network, results in further expense and disruption to the customers.

Figure 6:
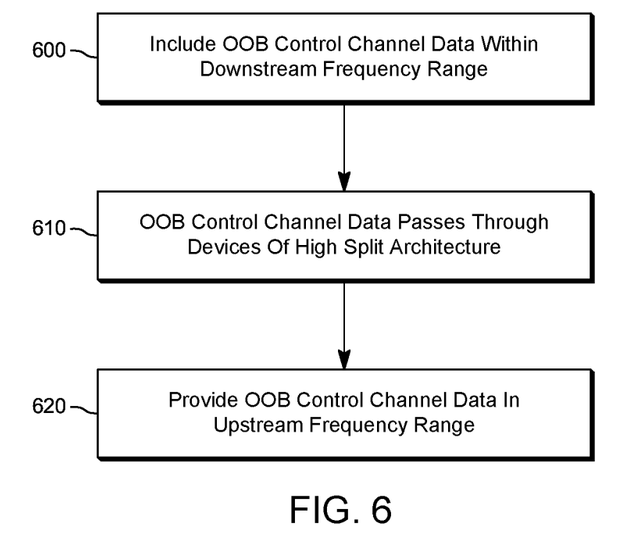
FIG. 6 illustrates receiving and transmitting OOB signals.

Referring to FIG. 6, the OOB control channel data may be included in a carrier frequency or channel within the downstream frequency range 600. With the OOB control channel data included within the downstream frequency range 600, the OOB control channel data may pass through the existing high split architectures 610, inclusive of the amplifiers, the splitters, and the taps. This may be achieved in any suitable manner, such as frequency conversion of an existing OOB signal, direct generation of the same signal but in the downstream frequency range, or by including the OOB control channel data in a downstream DOCSIS channel. The legacy consumer premise equipment still expect to receive the OOB control channel data at a predefined frequency, such as within the 70-130 MHz range, which is in the upstream frequency range of the network. It was determined that the OOB control channel data could be provided to the consumer premise equipment if it was included in the upstream frequency range in a manner that could be received by the legacy consumer premise equipment 620.

Figure 7:
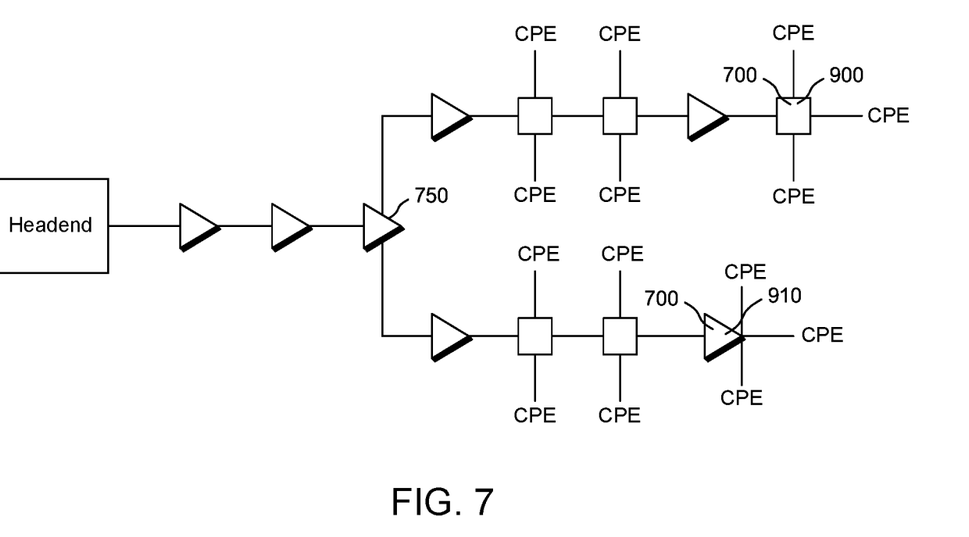
FIG. 7 illustrates another cable network with amplifiers, taps, and consumer premise equipment.

Referring to FIG. 7, to provide such OOB control channel data to the consumer premise equipment, the end of the line device of any particular branch of the network, such as one or more amplifiers and/or one or more taps, and/or otherwise may be used in a different manner, generally referred to herein as an end of the line device 700.

Figure 8:
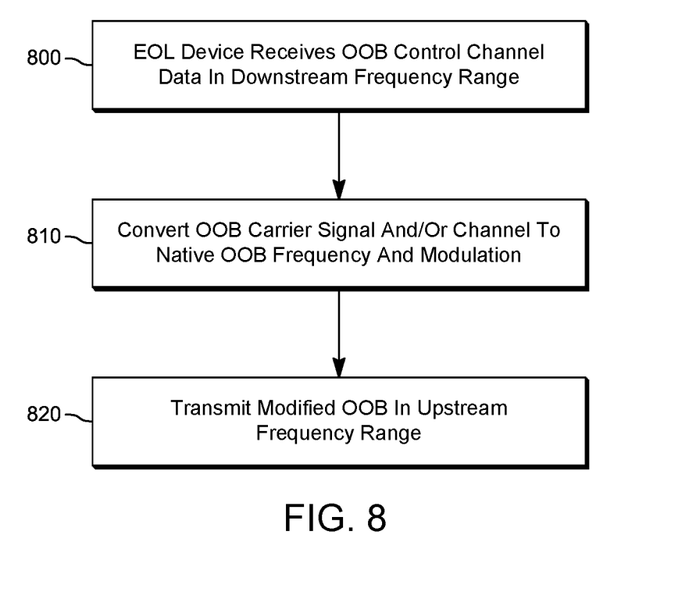
FIG. 8 illustrates modifying OOB signals.

Referring also to FIG. 8, the end of the line device 800 receives the OOB control channel data in the downstream frequency range. The end of the line device 800 converts the OOB carrier signal and/or channel to a natively supported OOB frequency and modulation format in a suitable manner 810, such as using a frequency and/or a modulation and/or a data conversion technique. For example, the resulting OOB control channel data may be a 2 MHz QPSK signal within the 70 to 130 MHz range, which is in the upstream frequency spectrum of the high split architecture. The end of line device 800 transmits the modified OOB signal in the upstream data path 820 within the upstream frequency spectrum to devices which are interconnected to the network, which includes any customer premise equipment interconnected to the end of the line device 700 and to other amplifier, splitters, and taps to which may be interconnected to customer premise equipment. It is noted that the amplifiers, splitters, and taps in the upstream data path are designed to pass the OOB signal within this frequency range along with any other data included within the upstream frequency spectrum. The OOB control channel data will be received by the customer premise equipment through the tap-output leakage of the taps, which is generally 10-14 dB higher than the tap loss. Also, the OOB signal is preferably scaled to a greater magnitude than it would otherwise be scaled to, in order to accommodate the increased loss as a result of the tap. It is noted that for customer premise equipment that are not interconnected through a tap relative to the end of the line device 700, similar scaling of the increased magnitude is not necessary. It is further noted that the signal path from the end of line device (e.g., amplifier) to any given upstream consumer premise equipment, the increase in loss is not cumulative, rather, it is only encountered once. The consumer premise equipment receives the OOB control channel data at the OOB frequency that it is expecting, and in this manner, the network does not need to be substantially modified to accommodate legacy consumer premise equipment.

As illustrated in FIG. 7, the amplifier 750 may include multiple outputs, each of which extends to a corresponding end of the line device 900, 910. Each end of line device 900, 910 generates a corresponding out of band signal with control data that is provided in the upstream data path. With each OOB signal having the same frequency, the amplifier 900 will receive multiple OOB signals, one from each end of line device 900, 910 which may result in undesirable interference. To overcome such interference, it is desirable to define a primary path and a secondary path (or additional paths) in the network. The primary path is preferably either that with the longest amplifier cascade or the largest service group, and the secondary path(s) are the path(s) other than the primary path. With multiple paths defined within the network, there are multiple techniques that may be used to manage the resulting OOB signals.

A first technique is to include a band-reject filter in each secondary path at the OOB frequency. This prevents the secondary OOB signal copies from interfering with the primary OOB signal. However, the band rejection filter makes the exclusion zone on these paths wider than is otherwise desirable and inhibits frequency agility in these paths.

A second technique is to include different primary and secondary OOB frequencies. The secondary OOB signals will not interfere with the primary OOB signals because of the frequency separation. The different secondaries will not substantially interfere with each other because of the combination of return loss, tap reverse isolation, line loss, and diplexer loss. In other words, while the different secondary OOB signals may interfere with each other, but this tends to occur only in the primary path, where it does not have a substantial impact on performance. The primary path will not interfere with the secondary paths for corresponding reasons, in conjunction with the frequency isolation. In general, the system may use twice the exclusion zone for a single end of line device OOB without band rejection filters. Without the band rejection frequency that exclusion zone is naturally smaller. Using a 3 MHz exclusion zone for each OOB may be used, with is a 6 MHz exclusion zone for the primary and the secondary signals.

The end of line architecture enables several advantages. One advantage includes potentially fewer modules to deploy in fewer physical locations, which results in fewer deployments of the service truck. With only a conversion module at each end of line device and a single band rejection filter at each line junction, deployment is simplified, and manually setting the frequency and level is simplified.

Another advantage is less steep filtering band rejection filter requirements as the filters are only needed to prevent self-interference between different conversion modules, as opposed to a filter that addresses loop gain concerns. In this manner, they can be simpler and smaller, with fewer components, than the ones used for the forward bypass technique.

Another advantage is a reduction or otherwise elimination of cascading problems. Both the bypass approach and forward frequency conversion approach include a band rejection filter at each amplifier, which effectively widens the exclusion zone in proportion to the cascade depth. In the end of line approach, adjacent upstream signals will see a maximum of 1 band rejection filter, so the exclusion zone is minimized. For the primary path with no band rejection filter, the exclusion zone is generally only limited by the OOB channel width and frequency tolerance. Also, the overall signal level is primarily dependent on the upstream/downstream paths, which try to maintain the proper levels. The primary independent gains and/or losses are the reverse tap isolations and the conversion gain of the end of line device. Utilizing the existing gain control results in only one attenuator to be suitably determined per end of line device, instead of one attenuator per amp (levels get more difficult to control over the full cascade). Also, the upstream receiver of the node sees the full OOB signal and can determine the received level and compensate by boosting the level of the upconverted OOB signal.

Another advantage includes some frequency agility of native OOB signal, if it's suitable to lose some upstream bandwidth. In the primary upstream path, the frequency range is determined by the response of the filter following the mixer (could be band pass filter or low pass filter). Because this path doesn't see any band rejection filters, the OOB may run the entire range of that mixer filter. In the secondary paths, the frequency is fixed by the band rejection filter response and defined dead zone. So, the primary path is somewhat frequency agile, but may require an additional dead zone on the modems in the secondary paths. The secondary path's native frequency doesn't have to match the primary paths, though, which provides another element of frequency agility.

Another advantage includes potentially eliminating band rejection filters entirely by using a first OOB frequency for the primary path, a second OOB frequency for all secondary paths, and 2-3 MHz exclusion zones everywhere.

Moreover, each functional block or various features in each of the aforementioned embodiments may be implemented or executed by a circuitry, which is typically an integrated circuit or a plurality of integrated circuits. The circuitry designed to execute the functions described in the present specification may comprise a general-purpose processor, a digital signal processor (DSP), an application specific or general application integrated circuit (ASIC), a field programmable gate array (FPGA), or other programmable logic devices, discrete gates or transistor logic, or a discrete hardware component, or a combination thereof. The general-purpose processor may be a microprocessor, or alternatively, the processor may be a conventional processor, a controller, a microcontroller or a state machine. The general-purpose processor or each circuit described above may be configured by a digital circuit or may be configured by an analogue circuit. Further, when a technology of making into an integrated circuit superseding integrated circuits at the present time appears due to advancement of a semiconductor technology, the integrated circuit by this technology is also able to be used.

It will be appreciated that the invention is not restricted to the particular embodiment that has been described, and that variations may be made therein without departing from the scope of the invention as defined in the appended claims, as interpreted in accordance with principles of prevailing law, including the doctrine of equivalents or any other principle that enlarges the enforceable scope of a claim beyond its literal scope. Unless the context indicates otherwise, a reference in a claim to the number of instances of an element, be it a reference to one instance or more than one instance, requires at least the stated number of instances of the element but is not intended to exclude from the scope of the claim a structure or method having more instances of that element than stated. The word "comprise" or a derivative thereof, when used in a claim, is used in a nonexclusive sense that is not intended to exclude the presence of other elements or steps in a claimed structure or method.

We claim:

1. A method comprising:
   (a) at a downstream end of line device, where said downstream end of line device receives downstream signals within a downstream frequency range from a head end, where said downstream end of line device provides upstream signals within an upstream frequency range to said head end, where said downstream end of line device provides downstream signals within said downstream frequency range to consumer premise equipment, where said downstream end of line device receives upstream signals within an upstream frequency range from said consumer premise equipment, modifying an out-of-band signal received from said head end in a downstream frequency of said downstream frequency range that includes control channel data for said consumer premise equipment to an out-of-band signal for an upstream frequency within said upstream frequency range for said consumer premise equipment;
   (b) transmitting said modified out-of-band signal to said consumer premise equipment from said end of line device within said upstream frequency within said upstream frequency range as part of said upstream signals within said upstream frequency range to said head end, where said modified out-of-band signals is scaled to a greater magnitude than other signals of said upstream signals in a manner such that said modified out-of-band signals are suitable for being received by said consumer premise equipment through tap-output leakage of a tap interconnected to said consumer premise equipment;

(c) wherein said out-of-band signal received in said downstream frequency by said downstream end of line device comprises a frequency that is above a guard band for a cable television system downstream communications band; and (d) wherein said modified out-of-band signal transmitted by said downstream end of line device in said upstream frequency within said upstream frequency range comprises a frequency that is below said guard band for said cable television system upstream communications band.

2. The method of claim 1 wherein said out-of-band signal received by said end of line device being in a range greater than 200 MHz.

3. The method of claim 1 wherein said out-of-band signal transmitted by said end of line device being in a range of 70 MHz to 130 MHz.

4. The method of claim 3 wherein said out-of-band signal includes control channel data.

5. The method of claim 4 wherein said control channel data includes a channel map.

6. The method of claim 5 wherein said transmitted out-of-band signal is a QPSK signal.

7. The method of claim 6 wherein said transmitted out-of-band signal is received by said customer premise equipment though a tap-output isolation of a tap.

8. The method of claim 6 further comprising a plurality of said end of line devices and each of said devices receiving a corresponding said out-of-band signal received in said downstream frequency at a different frequency.

\* \* \* \* \*